(12) United States Patent
Baillargeon et al.

(10) Patent No.: US 12,376,734 B2
(45) Date of Patent: Aug. 5, 2025

(54) TIP ASSEMBLIES FOR REAL-TIME SAMPLING SYSTEM

(71) Applicant: OLYMPUS MEDICAL SYSTEMS CORPORATION, Hachioji (JP)

(72) Inventors: Jean-Martin Baillargeon, Seattle, WA (US); Jason T. Panzenbeck, Seattle, WA (US); Peter A. Lambe, Redmond, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 747 days.

(21) Appl. No.: 17/493,320

(22) Filed: Oct. 4, 2021

(65) Prior Publication Data

US 2022/0133264 A1    May 5, 2022

Related U.S. Application Data

(60) Provisional application No. 63/109,558, filed on Nov. 4, 2020.

(51) Int. Cl.
*A61B 1/00* (2006.01)
*A61B 1/018* (2006.01)
(Continued)

(52) U.S. Cl.
CPC ...... *A61B 1/00066* (2013.01); *A61B 1/00137* (2013.01); *A61B 1/018* (2013.01);
(Continued)

(58) Field of Classification Search
CPC ....... A61B 1/00066; A61B 8/12; A61B 8/445; A61B 2017/3413; A61B 2090/3925; A61B 8/4444
See application file for complete search history.

(56) References Cited

U.S. PATENT DOCUMENTS

| 6,017,311 A * | 1/2000 | Sakamoto | A61B 8/12 |
| | | | 600/459 |
| 2002/0026187 A1* | 2/2002 | Swanson | A61B 18/1492 |
| | | | 606/41 |

(Continued)

FOREIGN PATENT DOCUMENTS

| CN | 114431894 A | 5/2022 |
| EP | 3995084 A1 | 5/2022 |

(Continued)

OTHER PUBLICATIONS

"European Application Serial No. 21204983.7, Response filed Oct. 27, 2022 to Extended European Search Report mailed Mar. 7, 2022", 9 pgs.

(Continued)

*Primary Examiner* — Amal Aly Farag
(74) *Attorney, Agent, or Firm* — Schwegman Lundberg & Woessner, P.A.

(57) ABSTRACT

An apparatus and system for effective real-time visualization of medical device usage. The apparatus includes a handle that receives a medical device and an imaging component, a flexible shaft includes at least two lumen and is attached to the handle and an end cap attached to the flexible shaft. The end cap includes a first lumen, an exit port located at a proximal end of the end cap, a first slot, and a second slot. The first lumen of the end cap receives the imaging component from the flexible shaft. The exit port receives the medical device from the flexible shaft. The slots are located longitudinally on an outer surface of the end cap at a distal section of the end cap. The first lumen of the end cap opens into a trough for better tissue connectivity.

16 Claims, 6 Drawing Sheets

(51) Int. Cl.
*A61B 1/267* (2006.01)
*A61B 8/00* (2006.01)
*A61B 8/08* (2006.01)
*A61B 8/12* (2006.01)
*A61B 17/34* (2006.01)
*A61B 90/00* (2016.01)

(52) U.S. Cl.
CPC .............. *A61B 1/2676* (2013.01); *A61B 8/12* (2013.01); *A61B 8/445* (2013.01); *A61B 2017/3413* (2013.01); *A61B 2090/3784* (2016.02); *A61B 2090/3925* (2016.02)

(56) References Cited

U.S. PATENT DOCUMENTS

| | | | |
|---|---|---|---|
| 2014/0296708 | A1 | 10/2014 | Flaherty et al. |
| 2019/0261946 | A1* | 8/2019 | Panzenbeck ...... A61M 25/0108 |
| 2020/0077975 | A1 | 3/2020 | Panzenbeck |
| 2020/0297311 | A1 | 9/2020 | Baillargeon et al. |
| 2020/0323419 | A1* | 10/2020 | Okada ................. A61B 1/0661 |

FOREIGN PATENT DOCUMENTS

| | | |
|---|---|---|
| JP | H0568517 | 3/1993 |
| JP | H0737108 | 2/1995 |
| JP | H1014858 | 1/1998 |
| JP | H10118070 | 5/1998 |
| JP | 2019150567 | 9/2019 |
| JP | 2022075595 A | 5/2022 |
| JP | 7410916 B2 | 12/2023 |

OTHER PUBLICATIONS

"Japanese Application Serial No. 2021-179422, Notification of Reasons for Rejection mailed Mar. 6, 2023", W English Translation, 8 pgs.

"Japanese Application Serial No. 2021-179422, Notification of Reasons for Rejection mailed Mar. 6, 2023", w english claims, 11 pgs.

"Japanese Application Serial No. 2021-179422, Notification of Reasons for Rejection mailed Jun. 26, 2023", w English Translation, 10 pgs.

"Japanese Application Serial No. 2021-179422, Response filed Sep. 20, 2023 to Notification of Reasons for Rejection mailed Jun. 26, 2023", w/o claims, 7 pgs.

Feb. 25, 2022, EP Intellectual Property Office issued a Search Report which cited references for European Patent Application No. 21204983.

"European Application Serial No. 21204983.7, Office Action mailed Mar. 24, 2022", 2 pgs.

"European Application Serial No. 21204983.7, Response filed Apr. 19, 2022 to Office Action mailed Mar. 24, 2022", 3 pgs.

* cited by examiner

TIP ASSEMBLIES FOR REAL-TIME SAMPLING SYSTEM

PRIORITY CLAIM

This application claims the benefit of U.S. Provisional Application No. 63/109,558, filed Nov. 4, 2020, the contents of which are hereby incorporated by reference.

BACKGROUND

FIG. 1 illustrates a distal end of an exemplary real-time sampling device. The distal end includes a probe lumen for receiving a radial ultrasound probe and two smaller lumens for receiving orientation pins. The pins reflect the ultrasound signals thus casting a shadow, as shown in FIG. 2.

SUMMARY

The present disclosure provides an exemplary system for effective real-time visualization of medical device usage. The system includes an imaging system having a radial ultrasound probe, an image processor in signal communication with the radial ultrasound probe, and a display configured to display ultrasound images based on signals received from the image processor. The system also includes an apparatus that includes a handle configured to receive a medical device and the radial ultrasound probe and a flexible shaft attached at a proximal end to the handle. The flexible shaft includes a first lumen configured to receive the radial ultrasound probe from the handle, and a second lumen configured to receive the medical device from the handle. The apparatus also includes an end cap attached to a distal end of the flexible shaft. The end cap includes a first lumen, an exit port located at a proximal end, a first slot, and a second slot. The first lumen of the end cap receives the radial ultrasound probe from the first lumen of the flexible shaft when the end cap is attached to the flexible shaft. The exit port receives the medical device from the second lumen of the flexible shaft when the end cap is attached to the flexible shaft. The slots are located longitudinally on an outer surface of the end cap at a distal section of the end cap.

In one aspect, at least one ultrasound reflecting material is located in each of the slots.

In another aspect, the apparatus includes a trough located at a distal end of the end cap. The trough receives the radial ultrasound probe from the first lumen of the end cap that is located at a proximal end of the end cap.

In yet another aspect, the slots are located on at least one surface of the end cap adjacent to the trough or on another surface of the end cap proximal to the trough. The slots may be located on a longitudinal half of the end cap that is opposite the other longitudinal half of the end cap that includes the exit port. The surfaces of the end cap that are adjacent to the trough are located on the longitudinal half of the end cap that includes the slots.

In still another aspect, the end cap includes a second port located at the distal end. The second port provides access to the first lumen of the end cap. The second port of the end cap has a smaller cross-sectional diameter than the first lumen of the end cap.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings.

DETAILED DESCRIPTION

The following description is merely illustrative in nature and is not intended to limit the present disclosure, application, or uses. The following description explains, by way of illustration only and not of limitation, various embodiments of devices and methods for providing a real-time system.

Figure 3:
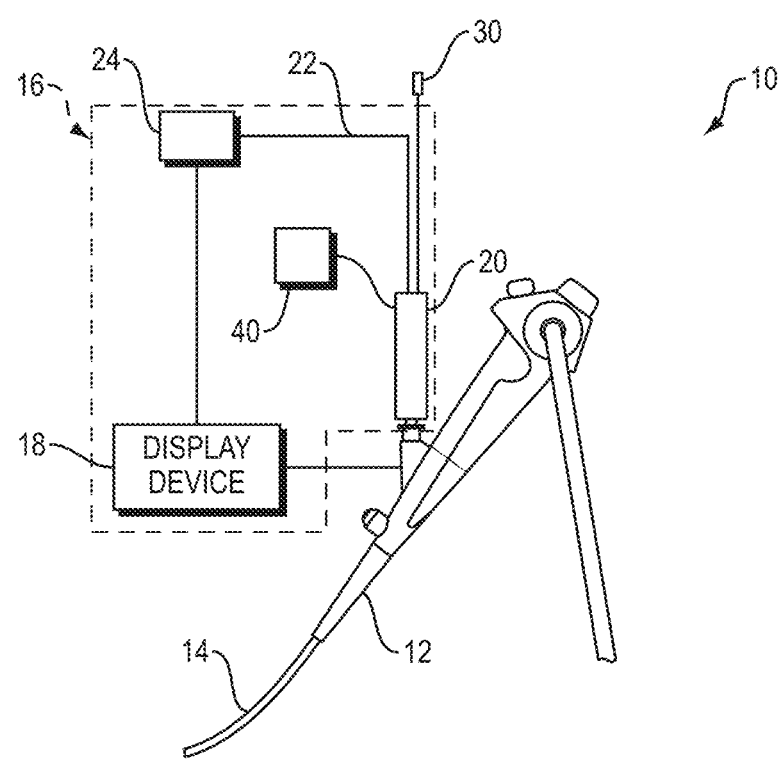
FIG. 3 illustrates an exemplary bronchoscope system with a real-time system.

Referring now to FIG. 3, a bronchoscope system 10 includes a bronchoscope 12 with an insertion tube 14, and a real-time system 16. A diagnostic bronchoscope (e.g., BF-P190 produced by Olympus®) is an example of the bronchoscope 12. The real-time system 16 includes a signal processor 24, a display device 18, a wire 22 connected to a radial ultrasound transducer (not shown) via a handle device 20. The real-time system 16 also includes a motor controller 40 connected to a distal motor (not shown) via the handle device 20.

The real-time system 16 includes a medical device 30, such as a needle for tissue sampling and/or medicant delivery that is slidably received within a lumen of a catheter (not shown). The catheter is attached at a proximal end to the handle device 20. The catheter is passed through the handle of the bronchoscope 12 and the insertion tube 14. The real-time system 16 may be used separate from the bronchoscope system 12.

The display device 18 is in wired or wireless signal communication with the signal processor 24. The display device 18 presents images based on image information received from the signal processor 24 that receives image information from a radial ultrasound transducer (not shown) of a radial ultrasound probe.

Figure 4:
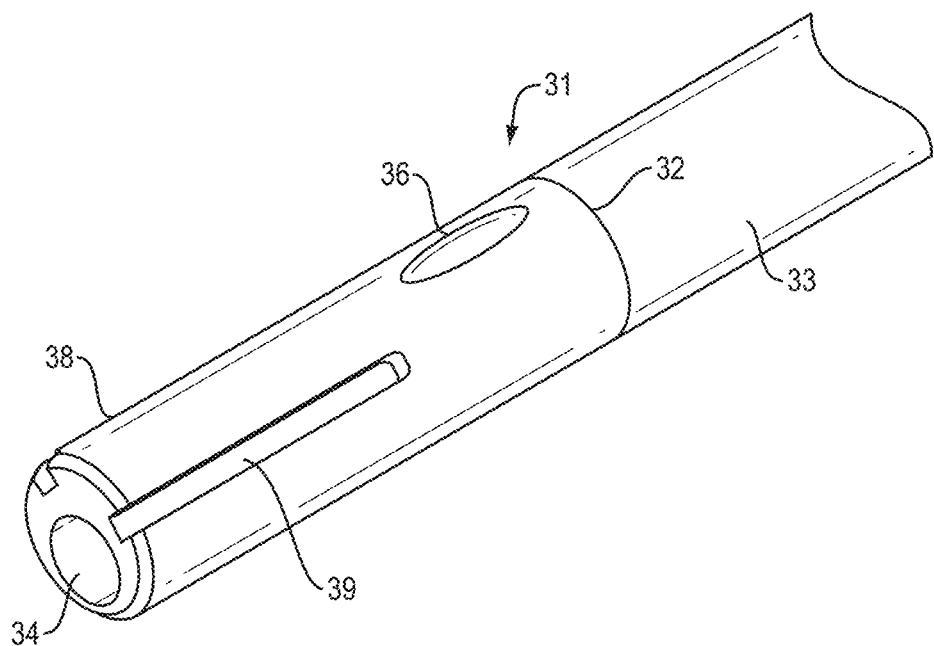
FIG. 4 is a perspective view of a distal end of a real-time system component formed in accordance with an embodiment.

FIG. 4 shows an exemplary end component 31 that is attached to a distal end 32 a flexible catheter 33. The flexible catheter 33 is attached to the handle device 20 at a proximal end and includes a lumen that is capable of receiving a radial ultrasound device and a smaller working channel for receiving the medical device 30 that is passed through the handle device 20. In one embodiment, the smaller working channel has an inner diameter that is less than half the inner diameter of the lumen that receives the radial ultrasound device. The end component 31 includes a first lumen 34 that is coaxial with the main lumen of the flexible catheter 33 when attached thereto. The first lumen 34 may be capped at the distal end in order to keep any ultrasound conducting fluid or gel within the lumen 34. The end component 31 includes an exit ramp 36 that allows the medical device 30 received within the working channel of the flexible catheter 33 to exit at a side of the end component 31 near a proximal end. The end component 31 may be attached to the flexible catheter 33 using epoxy, a thermal weld or a metal-to-metal weld. The ramp 36 could be made of steel while the ultrasound (i.e., US) window (i.e., portion of the end component 31) that surrounds where the probe is received is made of a plastic where the ramp 36 is welded to the braided material (not shown) of the sheath on the proximal end and the ramp 36 is epoxied to the US window on its distal end.

Figure 5:
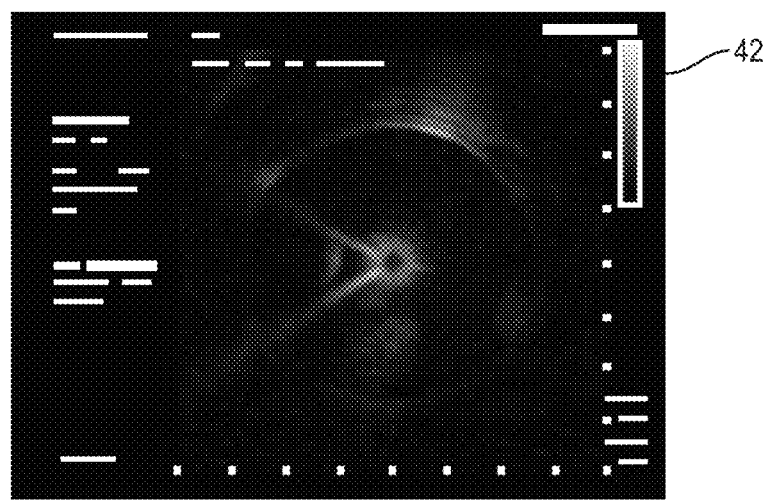
FIG. 5 shows an ultrasound image produced by a radial ultrasound device used within the component of FIG. 4.

The end component 31 includes two longitudinal slots (i.e., grooves) 38, 39 that extend from a distal end to a longitudinal point near the exit ramp 36. The slots 38, 39 are configured to receive ultrasound reflecting material, such as metal rods, flat wires, a high density film, metallic paint or another material that may be placed into the slots 38, 39. The material may be inserted into the slots 38, 39 in a molten or liquid state, then cooled to a solid-state. In one embodiment, stainless steel pins are used within the slots 38, 39 to provide orientation of the exit ramp 36 toward a target, as shown in ultrasound image 42 of FIG. 5. A centerline of the exit ramp 36 bisects the slots 38, 39.

Because the slots 38, 39 are located on the outer edge of the end component 31, the ultrasound reflections are more refined (i.e., minimal shadowing). Various angles between the slots 38, 39 may be used in order to provide the best balance of orientation and visibility of the medical device and the target. In one embodiment, the slots 38, 39 and/or the material within the slots 38, 39 has a width that is greater than or equal to 0.006" and less than or equal to 0.020".

The shape of the material within the slots 38, 39 can be flat-wired, rounded, hexagonal or parabolic in order to reflect ultrasound signals back towards a transducer of an ultrasound probe.

Figure 6:
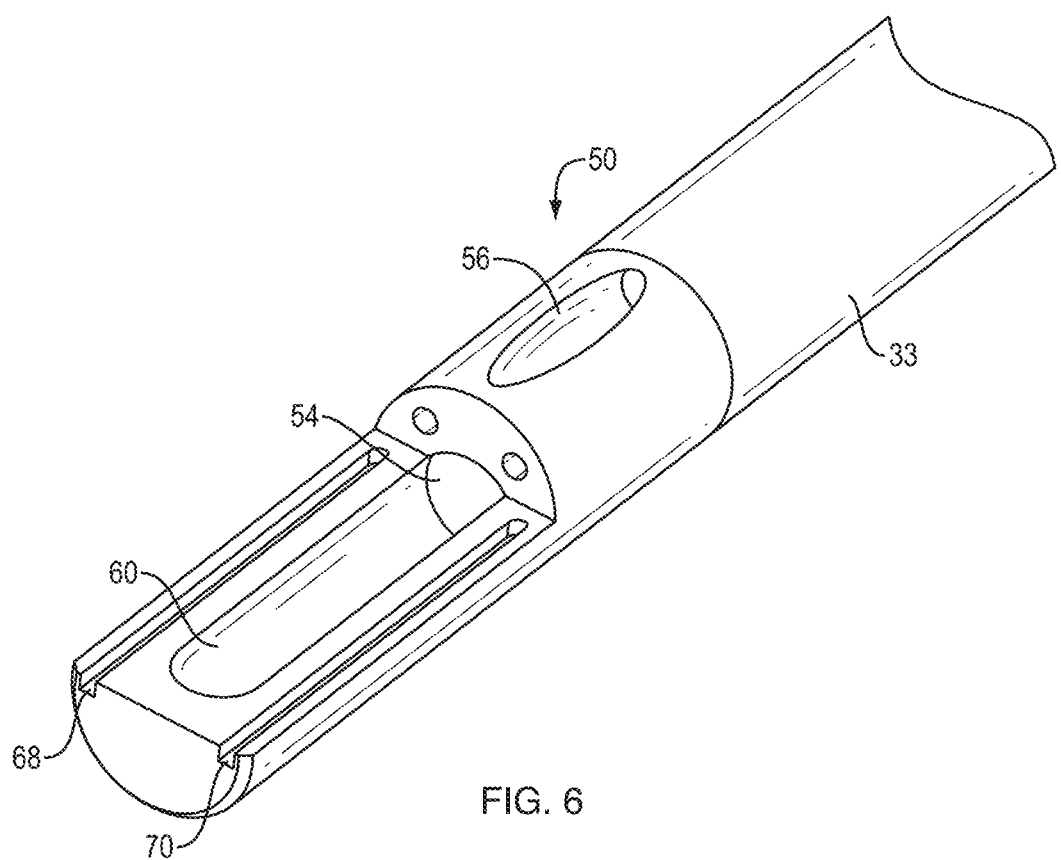
FIG. 6 is a perspective view of a distal end of a real-time system component formed in accordance with an embodiment.

As shown in FIG. 6, an end cap component 50 includes a proximal section that includes an exit ramp 56 that is positioned relative to the working channel of the flexible catheter 33. The end cap component 50 includes a distal section that includes a trough 60 that is coaxial with a lumen 54 of the proximal section all of which are coaxial with the lumen of the flexible catheter 33 that receives the ultrasound probe. The cross section of the distal section forms roughly a D-shape. This provides direct contact of the ultrasound probe with surrounding tissue. Adjacent to the trough 60 are slots (i.e., grooves) 68, 70 configured to receive ultrasound reflecting materials like the slots 38, 39 of FIG. 4.

Figure 7:
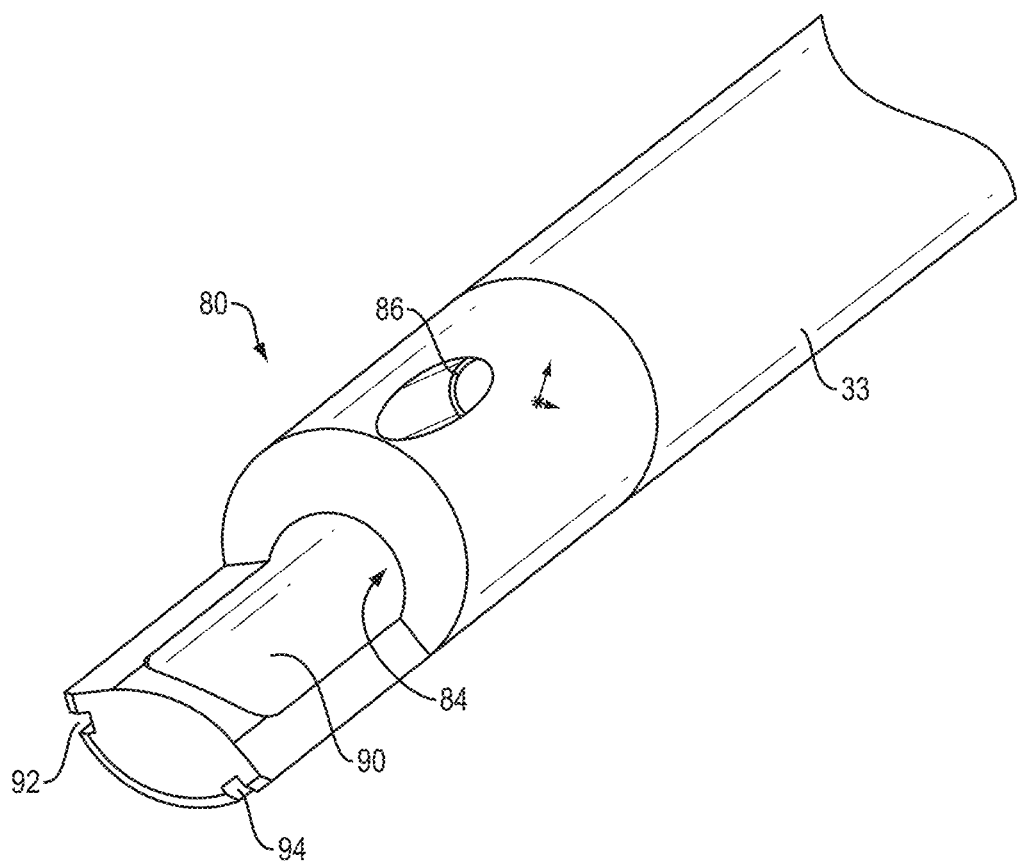
FIG. 7 is a perspective view of a distal end of a real-time system component formed in accordance with an embodiment.

As shown in FIG. 7, an end cap component 80 includes a proximal section that includes an exit ramp 86 that is positioned relative to the working channel of an attached flexible catheter 33 when attached thereto. The end cap component 80 includes a distal section that includes a trough 90 that is coaxial with a lumen 84 of the proximal section all of which are coaxial with the lumen of the flexible catheter 33 that receives the ultrasound probe. Less of the trough 90 is surrounded by material of the end cap component 80 than the trough 60 of the end cap component 50. Smaller slots (i.e., grooves) 92, 94 are located longitudinally in the outer rounded portion of the distal section and are configured to receive ultrasound reflecting materials like the slots 38, 39 of FIG. 4.

Figure 1:
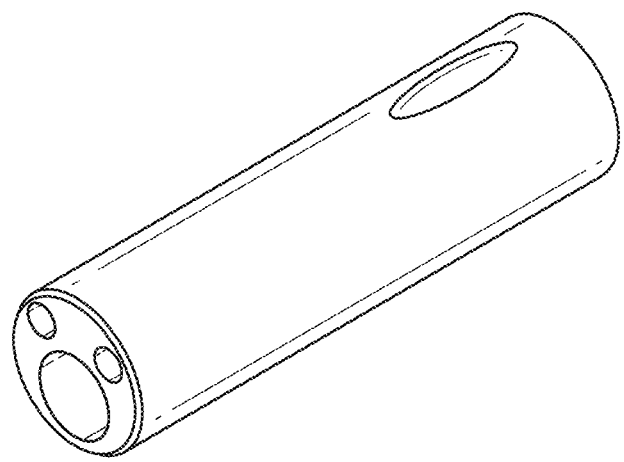
FIG. 1 is a perspective view of an end component formed in accordance with an embodiment of the prior art.
Figure 2:
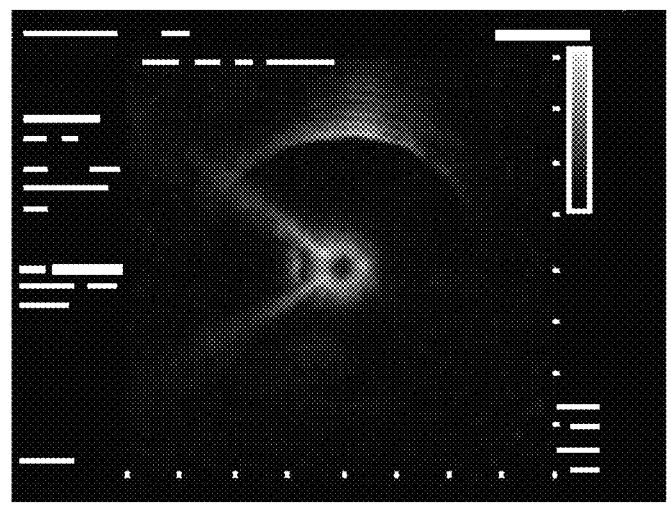
FIG. 2 shows an ultrasound image produced by a radial ultrasound device used within the end component of FIG. 1.
Figure 8:
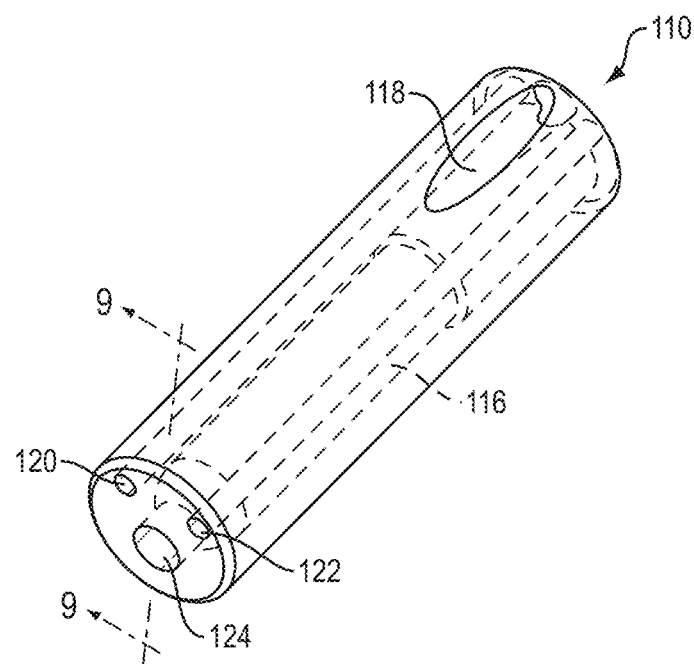
FIG. 8 is a perspective view of a distal end of a real-time system component formed in accordance with an embodiment.
Figure 9:
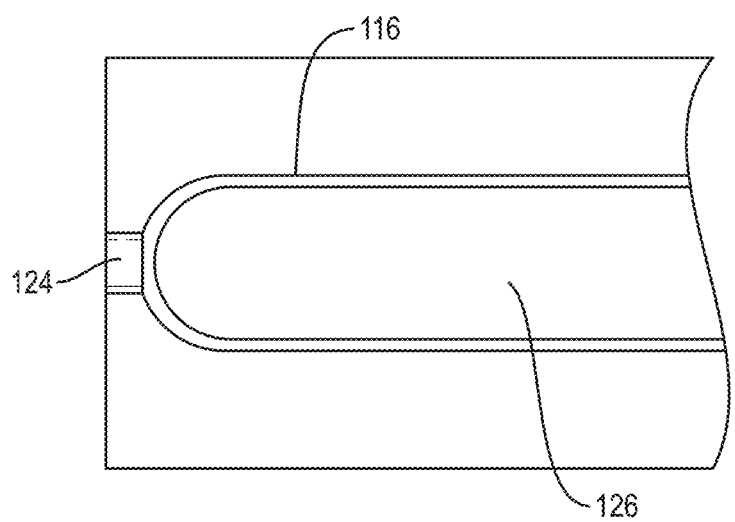
FIG. 9 is a cross-sectional view of the component of FIG. 8.

In one embodiment, as shown in FIGS. 8 and 9, an end cap component 110 includes a side port 118, orientation pin lumens 120, 122 and an ultrasound lumen 116 similar to that shown in FIG. 1. The orientation pin lumens 120, 122 may be filed with an ultrasound reflecting material, such as that described for FIG. 3 above, or may just include pockets of gas/air. The lumens 120, 122 may be open to surrounding environment, thus capturing air from the lung. However, the end cap component 110 includes a narrowed port 124 at the distal end for providing access to the ultrasound lumen 116. The port 124 allows for the injection of an ultrasound coupling fluid, such as a viscous gel (e.g., Aquasonic® 100). After injection of the ultrasound coupling fluid, an ultrasound probe 126 is inserted into the ultrasound lumen 116. Because the ultrasound probe 126 has a larger diameter than the port 124, the ultrasound coupling gel remains trapped within the ultrasound lumen 116.

Figure 10:
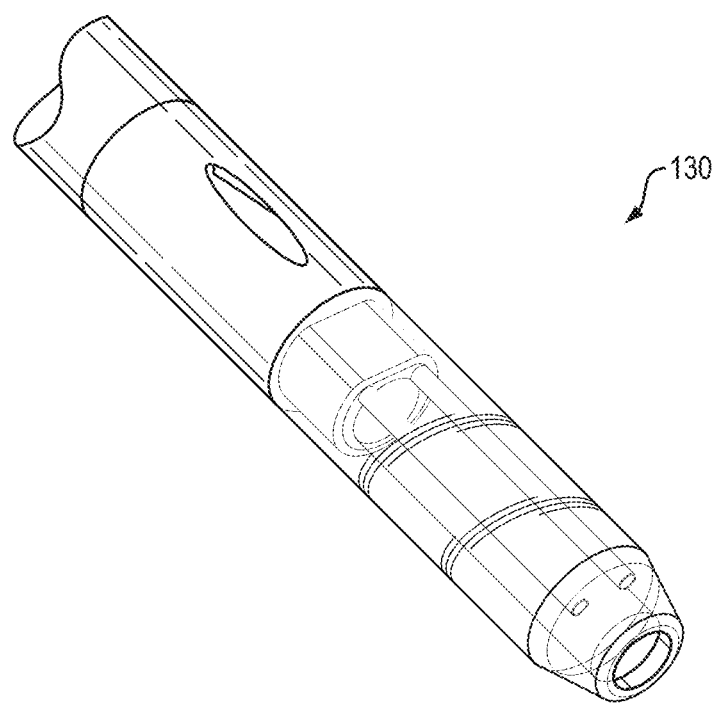
FIG. 10 is a perspective view of a distal end of a real-time system component formed in accordance with an embodiment.
Figure 11:
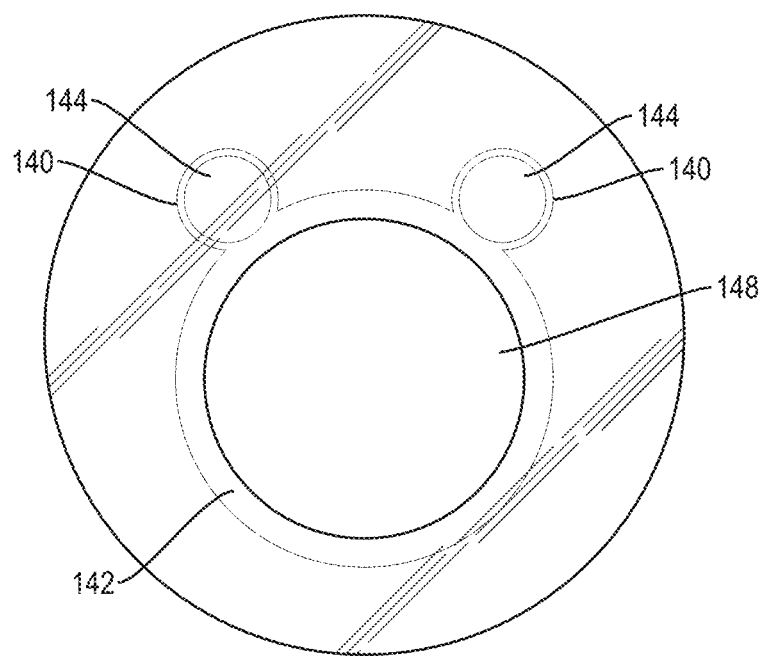
FIG. 11 is a cross-sectional view of the component of FIG. 10.

As shown in FIGS. 10 and 11, headlight lumens 140 are cut into a probe lumen 142 of an end cap 130, such that the material (i.e., headlights 144) placed in the headlight lumens 140 are exposed to the probe lumen 142. This allows the ultrasound coupling gel that is inserted into the probe lumen 142 to be in direct contact with the headlights 144, forming an ideal coupling for an US signal to reflect from the headlights 144 back to the US probe 148.

In one embodiment, the orientation pin lumens and slots that reflect ultrasound signals may have one or more longitudinal breaks (i.e., locations where no lumen or slot exists or no reflective material is used). Because of the breaks one can see in the ultrasound image where the transducer is located at the end cap. This happens because the ultrasound plane has a thickness in the longitudinal direction that is smaller than the length of the US window of the end cap.

The description of the invention is merely exemplary in nature and variations that do not depart from the gist of the invention are intended to be within the scope of the invention. Such variations are not to be regarded as a departure from the spirit and scope of the invention.

EMBODIMENTS

A. An apparatus comprising: a flexible shaft comprising: a first lumen; and a second lumen; and an end cap attached to a distal end of the flexible shaft, the end cap comprising: a first lumen; an exit port located at a proximal end of the end cap; a first slot; and a second slot, wherein the first lumen of the end cap is configured to receive an imaging tool from the first lumen of the flexible shaft when the end cap is attached to the flexible shaft, wherein the exit port is configured to receive a medical device from the second lumen of the flexible shaft when the end cap is attached to the flexible shaft, wherein the slots are located longitudinally on an outer surface of a distal section of the end cap.

B. The apparatus of A, further comprising an ultrasound reflecting material located in the slots.

C. The apparatus of A or B, wherein the imaging tool comprises a radial ultrasound probe.

D. The apparatus of any of A-C, further comprising a trough located at a distal end of the end cap, the trough being configured to receive the imaging tool from the first lumen of the end cap, wherein the first lumen of the end cap is located at a proximal end of the end cap.

E. The apparatus of D, wherein the slots are located on an outer surface of a portion of the end cap that includes the trough.

F. The apparatus of D or E, wherein the slots are located on a longitudinal half of the end cap that is opposite the other longitudinal half of the end cap that includes the exit port.

G. The apparatus of any of D-F, wherein the slots are located on a surface of the end cap adjacent to the trough.

H. The apparatus of G, wherein the surfaces of the end cap that are adjacent to the trough are located on the longitudinal half of the end cap that includes the slots.

I. The apparatus of any of A-C, further comprising a second port located at a distal end of the end cap, the second port provides access to the first lumen of the end cap.

J. The apparatus of I, wherein the second port of the end cap has a smaller cross-sectional diameter than the first lumen of the end cap.

K. A system comprising: an imaging system comprising: a radial ultrasound probe; an image processor in signal communication with the radial ultrasound probe; and a display configured to display ultrasound images based on signals received from the image processor; and an apparatus comprising: a handle configured to receive a medical device and the radial ultrasound probe; a flexible shaft attached at a proximal end to the handle comprising: a first lumen configured to receive the radial ultrasound probe from the handle; and a second lumen configured to receive the medical device from the handle; and an end cap attached to a distal end of the flexible shaft, the end cap comprising: a first lumen; an exit port located at a proximal end of the end cap; a first slot; and a second slot, wherein the first lumen of the end cap is configured to receive the radial ultrasound probe from the first lumen of the flexible shaft when the end cap is attached to the flexible shaft, wherein the exit port is configured to receive the medical device from the second lumen of the flexible shaft when the end cap is attached to the flexible shaft, wherein the slots are located longitudinally on an outer surface of the end cap at a distal section of the end cap.

L. The system of K, further comprising at least one ultrasound reflecting material located in each of the slots.

M. The system of K or L, wherein the apparatus further comprises a trough located at a distal end of the end cap, the trough being configured to receive the radial ultrasound probe from the first lumen of the end cap, wherein the first lumen of the end cap is located at a proximal end of the end cap.

N. The system of M, wherein the slots are located on at least one of a surface of the end cap adjacent to the trough or an outer surface of a portion of the end cap that includes the trough.

O. The system of M or N, wherein the slots are located on a longitudinal half of the end cap that is opposite the other longitudinal half of the end cap that includes the exit port.

P. The system of any of M-O, wherein the surfaces of the end cap that are adjacent to the trough are located on the longitudinal half of the end cap that includes the slots.

Q. The system of K or L, wherein the apparatus further comprises a second port located at a distal end of the end cap, the second port provides access to the first lumen of the end cap.

R. The system of Q, wherein the second port of the end cap has a smaller cross-sectional diameter than the first lumen of the end cap.

Although the preferable embodiments of the present invention have been described hitherto, the present invention is not limited to these embodiments. Additions, omissions, substitutions, and other modifications can be made without departing from the spirit or scope of the present invention.

What is claimed is:

1. An apparatus comprising:
a flexible shaft comprising:
a first lumen configured to receive a radial ultrasound probe; and
a second lumen;
an end cap attached to a distal end of the flexible shaft, the end cap comprising:
a cap lumen configured to receive the radial ultrasound probe from the first lumen;
an exit port located at a proximal end of the end cap, the exit port configured to receive a medical device from the second lumen of the flexible shaft when the end cap is attached to the flexible shaft;
a first slot including a first elongated groove disposed in an outer surface of the end cap;
a second slot including a second elongated groove disposed in an outer surface of the end cap;
a first ultrasound reflecting material disposed in the first slot; and
a second ultrasound reflecting material disposed in the second slot,
wherein the first slot and the second slot are positioned on the outer surface to provide an indication of orientation of the exit port within an output from the radial ultrasound probe.

2. The apparatus of claim 1, wherein at least one of the first ultrasound reflecting material or the second ultrasound reflecting material includes a concave side.

3. The apparatus of claim 1, wherein the first slot and the second slot are disposed on a same half of the end cap.

4. The apparatus of claim 3, wherein a center line of the exit port is disposed between the first slot and the second slot.

5. An apparatus comprising:
a handle configured to receive a medical device and a radial ultrasound probe;
a flexible shaft attached at a proximal end to the handle comprising:
a first lumen configured to receive the radial ultrasound probe from the handle; and
a second lumen configured to receive the medical device from the handle; and
an end cap attached to a distal end of the flexible shaft, the end cap comprising:
a first lumen;
an exit port located at a proximal end of the end cap;
a first slot including a first elongated groove disposed in an outer surface of the end cap; and
a second slot including a second elongate groove disposed in an outer surface of the end cap,
wherein the first lumen of the end cap is configured to receive the radial ultrasound probe from the first lumen of the flexible shaft when the end cap is attached to the flexible shaft,
wherein the exit port is configured to receive the medical device from the second lumen of the flexible shaft when the end cap is attached to the flexible shaft,
wherein the slots are located longitudinally on an outer surface of the end cap at a distal section of the end cap and positioned on the outer surface to provide an indication of orientation of the exit port within an output from the radial ultrasound probe.

6. The apparatus of claim 5, further comprising at least one ultrasound reflecting material located in each of the slots.

7. The apparatus of claim 5, wherein the apparatus further comprises a trough located at a distal end of the end cap, the trough being configured to receive the radial ultrasound probe from the first lumen of the end cap, wherein the first lumen of the end cap is located at a proximal end of the end cap.

8. The apparatus of claim 7, wherein the slots are located on at least one of a surface of the end cap adjacent to the trough or an outer surface of a portion of the end cap that includes the trough.

9. The apparatus of claim 8, wherein the slots are located on a longitudinal half of the end cap that is opposite the other longitudinal half of the end cap that includes the exit port.

10. The apparatus of claim 9, wherein the surfaces of the end cap that are adjacent to the trough are located on the longitudinal half of the end cap that includes the slots.

11. An apparatus comprising:
a flexible shaft comprising:
a first lumen configured to receive a radial ultrasound probe; and
a second lumen;
an end cap attached to a distal end of the flexible shaft, the end cap comprising:
a first lumen configured to receive the radial ultrasound probe;
an exit port located at a proximal end of the end cap, the exit port configured to receive a medical device from the second lumen of the flexible shaft when the end cap is attached to the flexible shaft;
an open slot including a first elongated groove disposed in an outer surface of the end cap; and
an ultrasound reflecting material disposed in the open slot, wherein the open slot is positioned on the outer surface to provide an indication of orientation of the exit port within an output from the radial ultrasound probe.

12. The apparatus of claim 11, wherein the end cap includes a second open slot including a second elongated groove disposed in an outer surface of the end cap.

13. The apparatus of claim 12, wherein the open slot and the second open slot are disposed on a same half of the end cap.

14. The apparatus of claim 13, wherein a center line of the exit port is disposed between the open slot and the second open slot.

15. The apparatus of claim 11, wherein the first elongated groove extends from a distal most end to a proximal position adjacent the exit port.

16. The apparatus of claim 1, wherein the first elongated groove and the second elongated groove extend from a distal most end to a proximal position adjacent the exit port.

* * * * *